United States Patent
Balchunas

(10) Patent No.: US 10,371,624 B2
(45) Date of Patent: Aug. 6, 2019

(54) INDEX OF REFRACTION SENSOR SYSTEM WITH DUAL MODE TEMPERATURE CONTROL

(71) Applicant: Entegris, Inc., Billerica, MA (US)

(72) Inventor: John Anthony Balchunas, St. Paul, MN (US)

(73) Assignee: Entegris, Inc., Billerica, MA (US)

( * ) Notice: Subject to any disclaimer, the term of this patent is extended or adjusted under 35 U.S.C. 154(b) by 0 days.

(21) Appl. No.: 15/769,121

(22) PCT Filed: Oct. 24, 2016

(86) PCT No.: PCT/US2016/058421
§ 371 (c)(1),
(2) Date: Apr. 18, 2018

(87) PCT Pub. No.: WO2017/074855
PCT Pub. Date: May 4, 2017

(65) Prior Publication Data
US 2018/0299368 A1    Oct. 18, 2018

Related U.S. Application Data

(60) Provisional application No. 62/246,446, filed on Oct. 26, 2015.

(51) Int. Cl.
*G01N 21/55*    (2014.01)
*G01N 21/03*    (2006.01)
*G01N 21/41*    (2006.01)

(52) U.S. Cl.
CPC ..... *G01N 21/0332* (2013.01); *G01N 21/4133* (2013.01); *G01N 2021/414* (2013.01); *G01N 2201/1211* (2013.01)

(58) Field of Classification Search
CPC .... G01N 21/4133; G01N 21/41; G01N 21/45; G01N 33/54373; G01N 2021/4146; G01N 2021/4166; G01N 2021/434; G01N 2021/7773; G01N 21/05; G01N 21/253; G01N 21/3504; G01N 21/431; G01N 21/4788; G01N 21/774; G01N 21/7743; G01N 21/8422; G01N 2201/061;
(Continued)

(56) References Cited

U.S. PATENT DOCUMENTS 3,713,738 A    1/1973    Bernhardt
6,970,256 B1   11/2005   Jackson
(Continued)

FOREIGN PATENT DOCUMENTS

CN    104596989 A    5/2015
JP    H06273329 A    9/1994
JP    H08129004 A    5/1996

*Primary Examiner* — Michael P Stafira
(74) *Attorney, Agent, or Firm* — Entegris, Inc.

(57) ABSTRACT

A sensor system (100) utilizes temperature control systems (262) and methods to achieve and maintain a sample in a sample chamber (110) at a sampling temperature. Such sensor systems and methods may employ a dual mode temperature controller including a spike mode (SMC) controller (274) and a proportional-integral-derivative (PID) mode controller (272). Based on a temperature of the sample, the temperature controller of the sensor system can initially enter the spike mode or the PID mode.

15 Claims, 16 Drawing Sheets

(58) Field of Classification Search
CPC ...... G01N 33/225; G01N 33/53; G01N 15/06; G01N 15/0656; G01N 15/1463; G01N 2015/0065; G01N 2015/0687; G01N 2015/0693; G01N 2015/1006; G01N 2015/1465; G01N 2015/1486; G01N 2021/0307; G01N 2021/0346; G01N 2021/058; G01N 2021/3509; G01N 2021/4126; G01N 2021/414; G01N 2021/437; G01N 2021/4709; G01N 2021/7759; G01N 2021/7783; G01N 2021/7796; G01N 2030/889; G01N 21/0303; G01N 21/19; G01N 21/27; G01N 21/31; G01N 21/3577; G01N 21/3581; G01N 21/43; G01N 21/47; G01N 21/554; G01N 21/7703; G01N 21/78; G01N 21/783; G01N 21/80; G01N 21/85; G01N 2201/0221; G01N 2201/06113; G01N 2201/062; G01N 2201/1211; G01N 2291/011; G01N 2291/021; G01N 2400/40; G01N 25/20; G01N 27/10; G01N 29/024; G01N 30/02; G01N 30/04; G01N 30/26; G01N 30/6052; G01N 30/74; G01N 30/8675; G01N 30/88; G01N 33/343; G01N 33/48735; G01N 33/4915; G01N 33/5302; G01N 33/536; G01N 33/57438; G01N 33/6803; G01N 9/00; G01N 9/26; G02B 1/14; G02B 5/3083; G02B 5/0242; G02B 5/26; G02B 1/04; G02B 5/02; G02B 5/0278; G02B 5/208; G02B 5/22; G02B 5/28; G02B 5/3033; G02B 1/005; G02B 1/11; G02B 1/111; G02B 1/115; G02B 1/12; G02B 27/0955; G02B 3/0087; G02B 5/0268; G02B 5/281; G02B 5/285; G02B 5/30; G02B 19/0052; G02B 1/02; G02B 1/041; G02B 1/043; G02B 1/10; G02B 1/105; G02B 1/118; G02B 2006/1213; G02B 21/0032; G02B 21/02; G02B 21/06; G02B 21/18; G02B 27/0172; G02B 27/0176; G02B 27/095; G02B 27/0977; G02B 27/283; G02B 3/005; G02B 3/0062; G02B 5/0221; G02B 5/0226; G02B 5/0247; G02B 5/0263; G02B 5/0284; G02B 5/0294; G02B 5/04; G02B 5/0841; G02B 5/122; G02B 5/18; G02B 5/20; G02B 5/283; G02B 5/3016; G02B 5/3025; G02B 5/32; G02B 6/00; G02B 6/0038; G02B 6/0051; G02B 6/0053; G02B 6/0061; G02B 6/0076; G01B 11/06; G01B 11/0625; G01B 9/02024; G01B 9/02041; G01B 9/02043; G01B 11/16; G01B 11/18; G01J 1/0477; G01J 1/4257; G01J 3/0208
See application file for complete search history.

(56) References Cited

U.S. PATENT DOCUMENTS

| | | | |
|---|---|---|---|
| 7,319,523 | B2 | 1/2008 | Chiarello et al. |
| 7,916,285 | B2 | 3/2011 | Amamiya et al. |
| 8,928,872 | B2 | 1/2015 | Muller et al. |
| 9,024,252 | B2 | 5/2015 | Chiarello et al. |
| 2005/0046853 | A1* | 3/2005 | Sato ............... G01N 21/553 356/445 |
| 2005/0213080 | A1* | 9/2005 | Huang ............. G01N 21/4133 356/128 |
| 2011/0122412 | A1 | 5/2011 | Joo et al. |
| 2012/0176627 | A1 | 7/2012 | Weinberger et al. |
| 2013/0155395 | A1* | 6/2013 | Muller ............. G01N 21/41 356/128 |

* cited by examiner

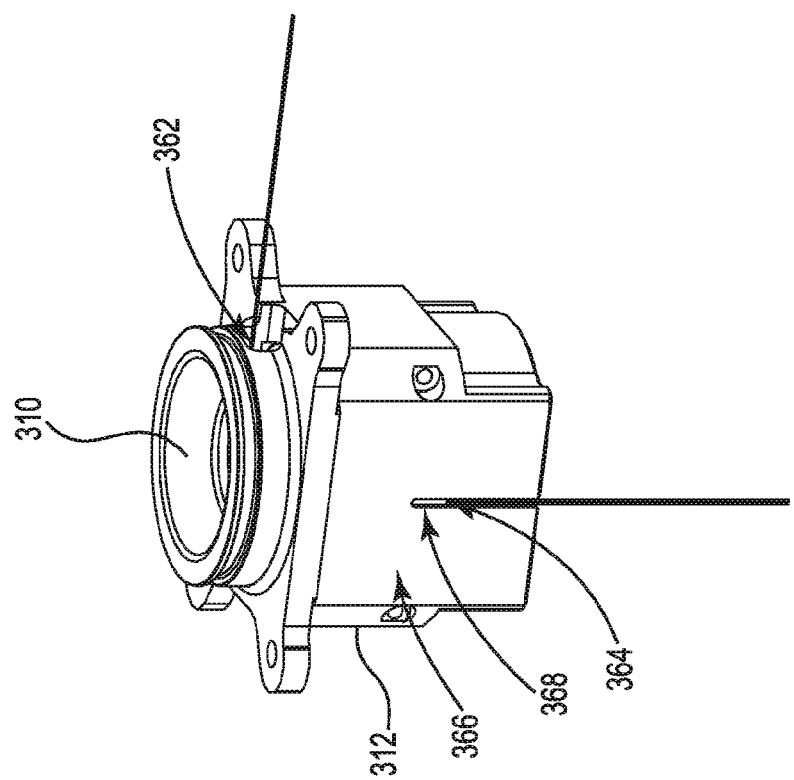

INDEX OF REFRACTION SENSOR SYSTEM WITH DUAL MODE TEMPERATURE CONTROL

RELATED APPLICATION

This application is a U.S. national phase under the provisions of 35 U.S.C. § 371 of International Patent Application No. PCT/US2016/058421 filed Oct. 24, 2016, which in turn claims the benefit of and priority to U.S. Provisional Application No. 62/246,446, filed on Oct. 26, 2015 and which are incorporated herein by reference, in their respective entireties, for all purposes.

TECHNICAL FIELD

Embodiments disclosed herein are related to sensor systems. In particular, embodiments are related to sensor systems that utilize optical sensors, including optical sensors that measure index of refraction of a sample. Even more specifically, embodiments are related to sensor systems that utilize optical sensors that measure index of refraction of a sample and include temperature control devices to achieve desired temperature of the sample.

BACKGROUND

Process analytical technology (PAT), as defined by the United States Food and Drug Administration (FDA), is a mechanism to design, analyze, and control pharmaceutical manufacturing processes through the measurement of Critical Process Parameters (CPP) which affect Critical Quality Attributes (CQA). By defining the CPPs, and then being able to monitor them quickly and accurately (preferably in-line or on-line), pharmaceutical companies, among others, are able to benefit from more efficient testing methods that lead to more consistent and efficient processes, whilst at the same time reducing risk.

Index of Refraction (IoR) sensors are examples of PAT, and are starting to see increased use in some critical process applications, such as media and buffer preparation, chromatography and clean-in-place (CIP) operations among others. These process steps require accurate liquid chemical concentration and temperature monitoring, as any mistakes can be very costly. Systems for refractive index measurement of a sample utilize principles of physics underlying the measurement of critical angle to determine refractive index of a medium. When light traveling from a high index medium is incident upon an interface between the high index medium and another medium having a lower refractive index at angles of incidence larger than a critical angle of incidence, total internal reflection may be observed. The critical angle is a function of the refractive index of both media. However, if the refractive index of one medium is known, the refractive index of the other may be determined from a measurement of the critical angle θc using a well-known formula. This refractive index measurement can correlate with a concentration of a species within a sample.

In some cases these IoR sensors have been utilized in processes such as those in the biotechnology and biopharmaceutical manufacturing markets. These type of processes include upstream applications such as mixing, clarification, and sterilizing filtration and downstream applications including cell harvesting, clarification, chromatography concentration and diafiltration, contaminant removal, and buffer preparation.

It is thus desired to provide standalone (also referred to as bench-top) IoR sensor systems that will enable entities to develop the PAT parameters for critical steps of their processes at bench scale (lab), early in a development cycle (e.g., for drug development). This will allow such entities to leverage the utility of such IoR sensors in multiple settings and more easily integrate the IoR measurements (or associated concentration measurements) into their processes, including their production processes.

SUMMARY

The present disclosure relates generally to sensor systems that utilize optical sensors that measure index of refraction of a sample and include temperature control devices to achieve desired temperature of the sample.

According to some embodiments, a sensor system for measuring the index of refraction of a sample includes a sample chamber for receiving a sample; a first temperature sensor coupled to the sample chamber; one or more heating and cooling elements coupled to the sample chamber; an index of refraction sensor exposed to the sample chamber, the sample chamber having a sampling temperature setpoint; and a system controller comprising a memory having the sampling temperature setpoint of the sample chamber stored therein, and a spike mode controller (SMC). The system controller is electronically coupled to and in communication with the first temperature sensor, the one or more heating and cooling elements and the index of refraction sensor, wherein if the system controller determines that a temperature of the sample chamber is outside the sampling temperature setpoint as measured by the first temperature sensor, the system controller is configured to activate the spike mode controller (SMC) to operate one or more heating and cooling elements to rapidly bring the temperature of the sample within the sampling temperature setpoint of the index of refraction sensor as determined by the first temperature sensor.

According to other embodiments, a method of measuring the index of refraction of a sample includes: 1)receiving a sample in a sampling chamber of sensor system, the sensor system comprising a system controller in electronic communication with first temperature sensor coupled to the sample chamber, one or more heating and cooling elements coupled to the sample chamber, and an index of refraction sensor exposed to the sample chamber, the system controller comprising a spike mode controller and a PID mode controller; 2) measuring a temperature of the sample via the temperature sensor; 3) determining if the temperature of the sample chamber is within a sampling temperature setpoint, 4) activating a spike mode controller (SMC) to operate one or more heating and cooling to reach a maximum hot or a maximum cold temperature if the system controller determines that a temperature of the sample is outside the sampling temperature setpoint as measured by the temperature sensor; 5) activating a PID mode controller to maintain the temperature of the sample within the sampling temperature setpoint if the system determines that the temperature of the sample is within the sampling temperature setpoint as measured by the first temperature setpoint; and 6) measuring an index of refraction of the sample when the temperature of the sample is within the sampling temperature setpoint.

In some cases, the sampling temperature setpoint is defined by upper and lower setpoints of the PID mode controller.

In still other cases, the sensor system as described herein may include a second temperature sensor coupled to the one or more heating elements.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various illustrative embodiments in connection with the accompanying drawings.

FIGS. 3A, 3B and 3C are different views of a bowl assembly with temperature sensors and heating/cooling element in accordance with an embodiment of the disclosure.

Figure 1A:
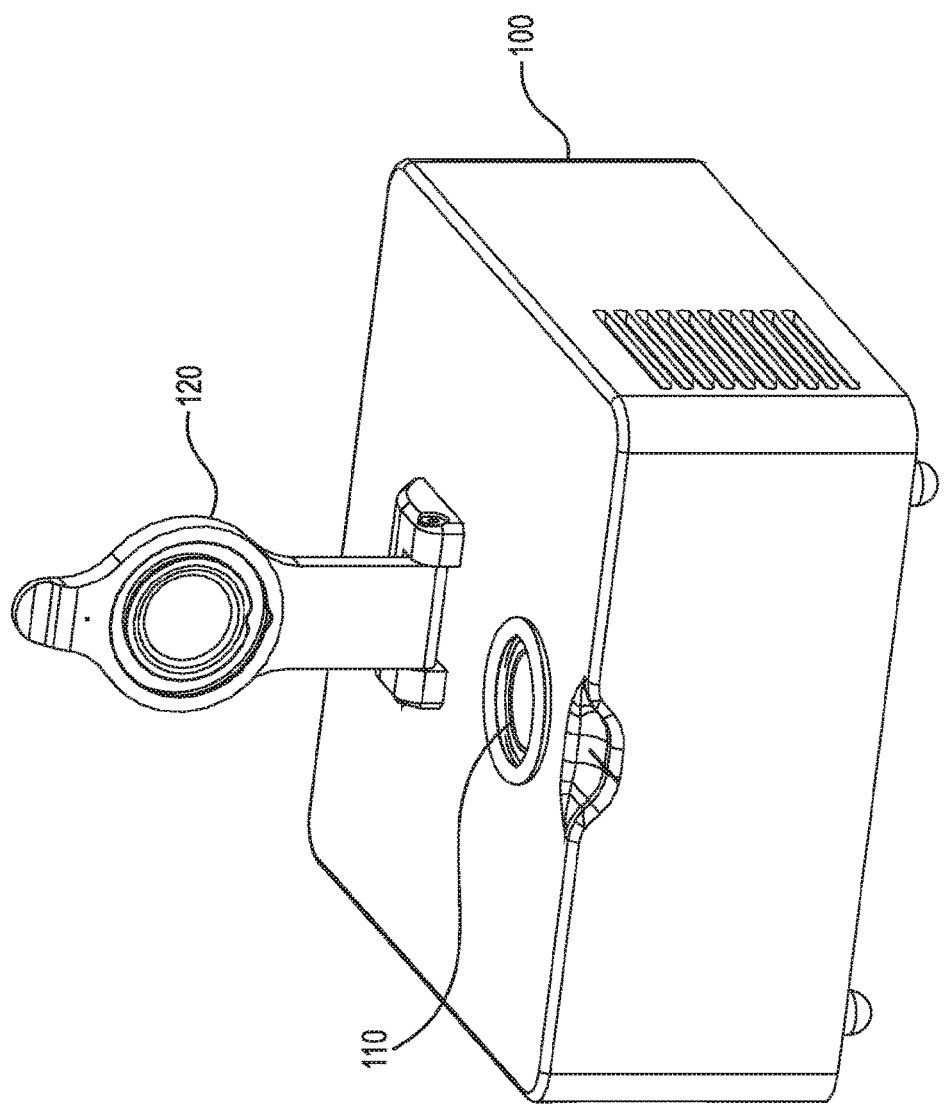
FIGS. 1A and 1B are schematic views of a bench-top index of refraction (IoR) sensor system in accordance with an embodiment of the disclosure

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The disclosure and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Embodiments of such a bench-top sensor may provide highly accurate IoR measurements of a sample. As is known, the temperature of the sample being measured affects any determination of concentration of a species derived from the IoR measured. At the same time, however, the introduction of a temperature compensation portion to the calculation of a concentration measurement increases the error of such calculations. Accordingly, it may be desired in some embodiments to hold the temperature of the sample undergoing measurement at a set temperature when taking the IoR measurement. In this manner, a pure IoR measure can be reported back to an operator (or utilized in a process). For example, most standard indices of refraction utilize 20 degrees Celsius as a standard temperature at which measurements of indices are reported.

In many cases, however, this desire may be difficult to accomplish in a real world setting. The samples desired to be measured may be extracted from many different types of processes and may be well outside the desired measurement temperature. Accordingly, it may take some time to achieve the desired temperature of the sample and take the desired measurement. What is desired are sensor systems that can provide accurate IoR measurements at a given temperature and which reduce the time needed for the sample undergoing measurement to reach such a temperature and take such an IoR measurement.

Accordingly, embodiments of a sensor system as disclosed herein may utilize temperature control systems and methods to achieve and maintain a sample in a sample chamber at a sampling temperature (or within a certain sampling tolerance of the sampling temperature, referred to as the sampling window). More specifically, embodiments of such sensor systems and methods may employ a dual mode temperature controller including a spike mode and a proportional-integral-derivative (PID) mode. Based on a temperature of the sample, the temperature controller of the sensor system can initially enter the spike mode or the PID mode.

Additionally, embodiments of a sensor system as disclosed herein may measure the IoR of a liquid in a process and include: one or more heating and cooling elements coupled to a sample chamber, a first temperature sensor coupled to the sample chamber and a second temperature sensor coupled to the one or more heating and cooling elements. The sensor system may also include a controller coupled to the first temperature sensor, the second temperature sensor, an IoR sensor exposed to the sample chamber, and the heating and cooling elements. The controller of the sensor system is operable to: determine whether a sample in the sample chamber sample is within a spike tolerance of a sampling temperature setpoint, spike the one or more heating and cooling elements with a high or maximum signal to the one or more heating and cooling elements if the temperature is not within the spike tolerance, maintain a temperature of the sample substantially at a sampling temperature setpoint, and measure the IoR of the sample within a sampling tolerance.

In one embodiment, if the temperature of the sample is within a spike tolerance (which may be different than the sampling tolerance) of the sampling temperature the temperature controller may enter the PID mode directly to maintain the temperature of the sample within the sample window. If, however, the temperature of the sample is outside the spike tolerance of the sampling temperature the temperature controller may enter the spike mode. In this spike mode, a heating or cooling device (which may be the same device) thermally coupled to the sample chamber may be activated at high or full power (e.g., to a maximum cold or hot setpoint) to more rapidly heat or cool the sample. In other words, if the sample is hotter than the sampling (or measurement) temperature plus the spike tolerance the cooling device may be activated at high or full power to cool the sample. Conversely, if the sample is colder than the sampling temperature minus the spike tolerance the heating device may be activated at high or full power to heat the sample. Once the heating or cooling element is at full power (e.g., at a maximum hot or cold setpoint) or it is determined the temperature of the sample is within the spike tolerance, the temperature controller may switch over to PID mode to maintain the temperature of the sample within the sample (or measurement) window.

For a variety of reasons it may be not be possible or desirable to have a temperature sensor in physical contact with the sample being measured. Accordingly, embodiments may utilize a first temperature sensor (referred to herein also as S1) placed in proximity to the sample chamber of the senor system. The temperature controller may utilize an initial temperature of the sample measured at this first temperature sensor to determine whether to enter spike mode or PID mode. Additionally, embodiments may utilize a second temperature sensor (referred to herein also as S2) placed in proximity to the heating or cooling device to measure the temperature at the point where thermal energy is being applied. In the PID mode the temperature controller may utilize the first temperature measured at the first temperature sensor and the second temperature measured at the second temperature sensor in controlling the heating or cooling devices to maintain the temperature of the sample within the sampling window. In a spike mode, the second temperature may be utilized to determine if full heating or cooling (e.g., a maximum hot or cold setpoint) has been achieved or the first temperature may be utilized to determine if the temperature is within the spike tolerance of the sampling window.

Figure 1B:
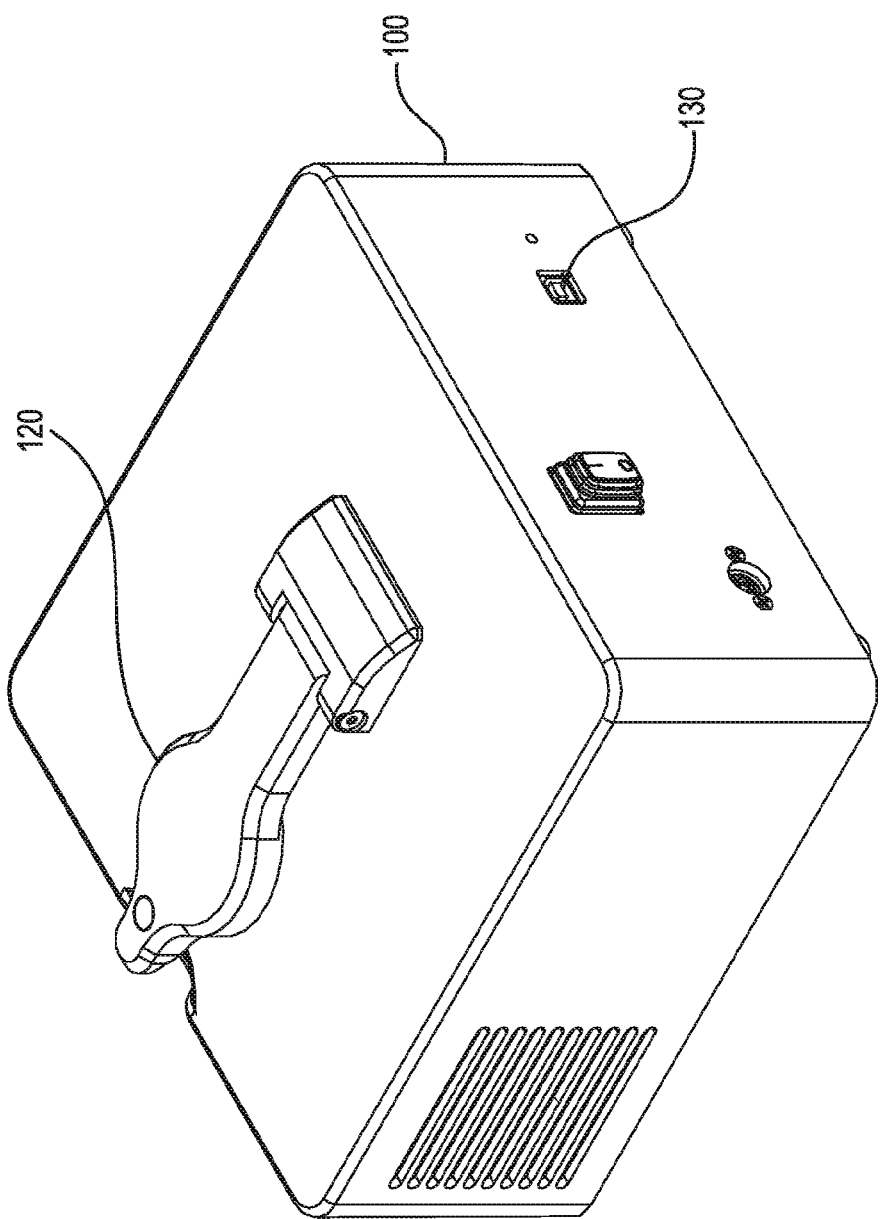

Turning first to FIGS. 1A and 1B, a representation of one embodiment of a bench-top index of refraction (IoR) sensor system is depicted. Sensor system 100 includes a sample chamber 110 and covering lid 120. An operator can lift lid 120 to access sample chamber 110 to place a sample to be measured therein and close lid 120. Additionally, sensor system 100 may include interface port 130 which may a USB, mini-USB, RS-232 interface or the like. Interface port 130 allows sensor system 100 to be coupled to an external computing device and may allow a system controller of the sensor system 100 to communicate with an external computing device to, for example, configure sensor system 100 or obtain an IoR measurement from sensor system 100.

Figure 2:
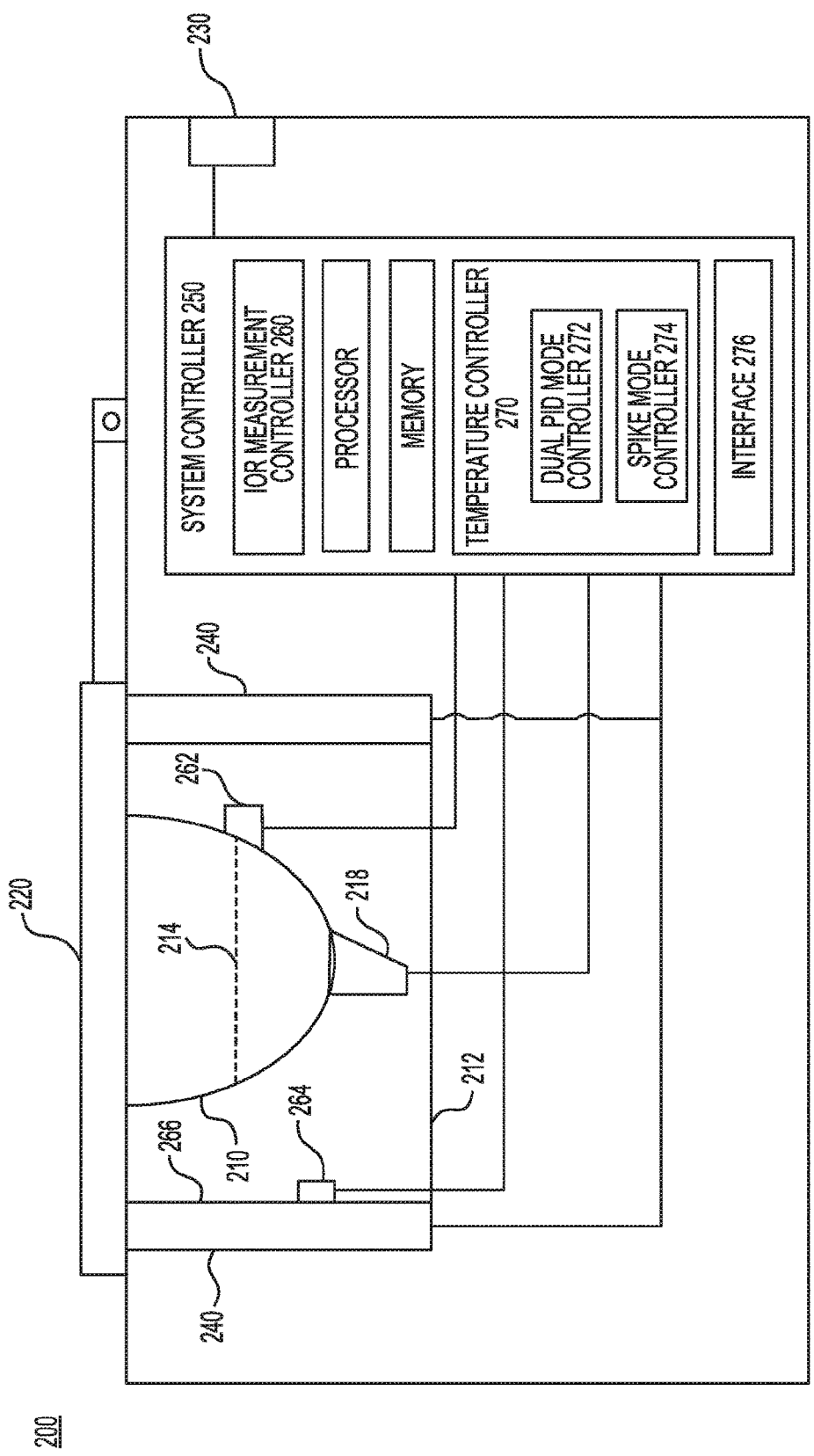
FIG. 2 is a block diagram of a bench-top IoR sensor system in accordance with an embodiment of the disclosure.

Moving now to FIG. 2 a block diagram of one embodiment of a bench-top IoR sensor system 200 is depicted. Again, sensor system 200 includes a sample chamber 210 and covering lid 220. An operator can lift lid 220 to access sample chamber 210 to place a sample to be measured therein and close lid 220. Sample chamber 210 is formed in bowl assembly 212. Index of Refraction (IoR) sensor 218 may interface with sample chamber 210. In particular, a seal may be formed between an optically transparent window of the sensor 218 and sample chamber 210 such that the optically transparent window of the sensor 218 is exposed to any sample in the sample chamber 210.

Bowl assembly 212 may, in one embodiment, be made of stainless steel. In other embodiments, bowl assembly 212 can be manufactured from non-reactive plastic or polymer materials such as perfluoroalkoxy polymer (PFA), polypropylene (PP) and polytetrafluoroethylene (PTFE), polyvinylidene fluoride, polyvinylidene difluoride (PVDF) or the like that are compliant with ultra-high purity environments including for example, those mandated by SEMI F57 specifications or the like. Additionally, bowl assembly 212 may be made of materials and dimensioned in almost any manner such that materials of bowl assembly 212 do not unduly inhibit heat transfer.

Sensor system 200 includes heating and cooling devices or elements 240 (collectively elements) thermally coupled to bowl assembly 212. In one embodiment, these heating or cooling elements 240 may be a part of a single device such as a thermoelectric cooler (also referred to as a Peltier device) including one element 240 coupled to one side of the bowl assembly 212 and a corresponding element 240 coupled to the opposite side of bowl assembly 212. Elements 240 may transfer heat from one side of the device to the other side with consumption of electrical energy depending on the direction of the current. These elements 240 may thus be configured to heat or cool bowl assembly 212 (and thus sample chamber 210 and any sample residing therein).

Sensor system 200 may also include a first temperature sensor 262, such as a thermistor or the like, thermally coupled to sample chamber 210. In one embodiment, the first temperature system 262 may be at a level that is substantially coplanar with the height of a minimum sample level required to be sample chamber 210 to achieve an accurate measurement of the sample therein. In some embodiments, first temperature sensor 262 may not be exposed to inside of sample chamber 210. Instead, there may be a portion of bowl assembly 212 between first temperature senor 262 and sample chamber 210 such that first temperature sensor 262 may be in close proximity to sample chamber 210 (and thus any sample therein). In one embodiment, for better thermal conductivity and to achieve greatest sensitivity in measuring temperature, or other reasons, it may be desired to place first temperature system 262 as close to sample chamber 210 as possible while still maintaining physical integrity of bowl 212 and sample chamber 210. Thus, the amount of bowl assembly 212 between first temperature system 262 and sample chamber 210 may depend on material of bowl assembly 212.

In cases where bowl assembly 210 is stainless steel, a counterbore may be created in bowl assembly 212 at the level of the minimum fluid level for a sample in sample chamber 210 such that 0.030 or less of an inch of bowl assembly 212 remains between first temperature system 262 and sample chamber 210. First temperature sensor 262 may be bonded to the bottom of such a counterbore using an adhesive. In embodiments this adhesive may be an epoxy or the like having a thermal connectivity which may be around 42 British Thermal Units (BTU)/inch/hour/square foot/degree Fahrenheit. As another example of an adhesive, a silver epoxy may be utilized. The use of silver epoxy may resist corrosion that may be caused by condensation on bowl assembly 212.

A second temperature sensor 264, such as a thermistor or the like, may be placed between a heating/cooling element 240 and bowl assembly 212 to detect the temperature at the point that thermal energy is being applied from element 240 to the bowl assembly 212. The second temperature sensor 264 can thus sense temperature of bowl assembly 212 at the location of greatest thermal conductivity between element 240 and sample chamber 210 with substantially minimal thermal lag.

Because of the nature of the element 240, to maximize transfer of thermal energy, or for other reasons it may be important to ensure that no irregularities (e.g., air gaps, surface bumps or pitting, etc.) exist between the element 240 and the surface 266 of the bowl assembly 212 to which it is to be coupled. Accordingly, in some embodiments, a trough or other channel may be formed below surface 266 in bowl assembly 212 and the second temperature sensor 264 (and any associated wiring or leads) placed therein. In this manner, surface 266 may remain substantially planar for better coupling of element 240 thereto. Additionally, for similar reasons, the use of a bonding agent, including thermally conductive bonding agents, to couple element 240 to bowl assembly 212 may not be desirable as the use of such bonding agents may also serve to create surface irregularities. Therefore, to ensure adequate thermal coupling of element 240 to bowl assembly 212 in certain embodiments a pad or plate (not shown) may be placed between element 240 and bowl assembly 212. Such a pad may be thermal graphite or the like having a substantially similar footprint to the element 240. In one embodiment, the pad may have a thickness of around 0.005 inches or the like. The element 240, pad and surface 266 of bowl assembly 212 may be aligned and mechanically coupled, using for example screws or other mechanical fasteners.

System controller 250 may be hardware or software or some combination of the two and may include interface 276, temperature controller 270 and IoR measurement controller 260. System controller 250 also can include a memory and a processor for executing one or more control algorithms stored in the memory of the controller 250. System controller 250 is configured to receive a first temperature measurement (e.g., measuring sample chamber temperature) from first temperature sensor 262 and a second temperature measurement from second temperature sensor 264 (e.g., indicating temperature at element 240). The system controller 250 is also configured to provide a control signal (e.g., current) to elements 240 to drive the elements 240, and to activate IoR sensor 218 and receive an IoR measurement from sensor 218 in return. Additionally, sensor system 200 may include interface port 230 which may a USB, mini-USB, RS-232 interface or the like. Interface port 230 allows sensor system 200 to be coupled to an external computing device and may allow a system controller 250 of the sensor system 200 to communicate with an external computing device.

Specifically, an operator at an external computer may configure a number of variables for use by system controller 250 using an external computer coupled to interface port 230. The variables are stored in the memory of the system controller 250. These variables may include, for example, a sampling temperature setpoint at which it desired to take an IoR measurement, a spike tolerance, a sampling tolerance, time windows to utilize in taking an IoR measurement (as will be discussed) or other variables. Alternatively, one or more of these variables may be determined by the manufacturer of the sensor system 200 and programmed or otherwise stored in the memory of the system controller 250 at a time of manufacture or calibration. In one embodiment, a sampling temperature setpoint may be between about 4 degrees Celsius and 40 degrees Celsius and in particular may be around 20 degrees Celsius. In certain embodiments, a spike tolerance may be around +/−0.5 degrees Celsius while the sampling tolerance may be around +/−0.2 degrees Celsius. Other sampling temperature setpoints, spike tolerances and sampling tolerances will be possible and are fully contemplated herein. It should also be noted that while embodiments have been described using an external computer coupled to interface port 230 it will be understood that other embodiments as contemplated herein may have such an interface built into or otherwise integrated with, the sensor system 200.

In embodiments, temperature controller 270 may include a dual PID mode controller 272 configured to maintain the sampling temperature setpoint based on a first temperature measured as first temperature sensor 262 and a second temperature measured at second temperature sensor 264. In some cases, the sampling temperature setpoint is defined by upper and lower PID mode controller temperature setpoints. In other words, in one embodiment, PID mode controller 272 is configured to sample temperatures from the first temperature sensor 262 and second temperature sensor 264 at some interval(s); derive a control signal for elements 240 based at least on these temperatures and the sampling temperature setpoint; and provide the determined control signal to elements 240 to maintain the temperature of the sample in chamber 210 (as measured by first temperature sensor 262) within the sampling tolerance of the sampling temperature setpoint. Temperature controller 270 also includes spike mode controller (SMC) 274 configured to control elements 240 to rapidly reach a maximum hot or maximum cold (e.g., a maximum hot or cold temperature setpoint) as determined based on a second temperature measured at second temperature sensor 264 or to determine if a first temperature measured at the first temperature sensor 262 is within a spike tolerance of the sampling temperature setpoint.

Accordingly, when a sample is placed in sample chamber 210 or when an operator at an external computer indicates through interface 276 that an IoR measurement is desired the temperature controller 270 may sample the first temperature as measured at first temperature sensor 262. If this first temperature is within the spike tolerance of the sampling temperature setpoint, the temperature controller may activate the dual PID mode controller 272 to control the temperature of the sample in the sample chamber 210. If, however, this first temperature is outside the spike tolerance (e.g., greater than the sampling temperature setpoint plus the spike tolerance or less than the sampling temperature setpoint minus the spike tolerance) the temperature controller may wait a delay time period (e.g., two seconds or the like) and again sample the first temperature as measured at first temperature sensor 262. If this first temperature is within the spike tolerance of the sampling temperature setpoint, the temperature controller may activate the dual PID mode controller 272 to control the temperature of the sample in the sample chamber 210. If, however, after this second temperature measurement, the first temperature is again outside the spike tolerance of the sampling temperature setpoint the temperature controller may activate the spike mode controller (SMC) 274 for a maximum hot setpoint (e.g., in cases where the measured temperature is below the sampling temperature setpoint minus the spike tolerance) or a maximum cold setpoint (e.g., in cases where the measured temperature is above the sampling temperature setpoint plus the spike tolerance). In one embodiment, the maximum setpoints may be 0 degrees Celsius and 60 degrees Celsius respectively. Spike mode controller (SMC) 274 then provides a control signal to elements 240 to drive the elements 240 until the proper setpoint (e.g., high or maximum cold or maximum hot) is achieved as determined by the spike mode controller (SMC) 274 based on a second measured temperature at the element 240 as received by spike mode controller (SMC) 274 from second temperature sensor 264. When the temperature measured at first temperature sensor 262 is within the spike tolerance of the sampling temperature setpoint, dual PID mode controller 272 may be activated to control the temperature of the sample in the sample chamber 210. In some cases, spike mode controller (SMC) 274 may drive heating and cooling elements 240 to heat or cool the chamber 210 such that the temperature of the sample chamber 210 is within the sampling temperature setpoint in less than about 10 minutes, in less than about 5 minutes, and more particularly in about 1 minute to about 5 minutes. This can reduce typical waiting times before an IoR measurement can be obtained.

Figure 10:
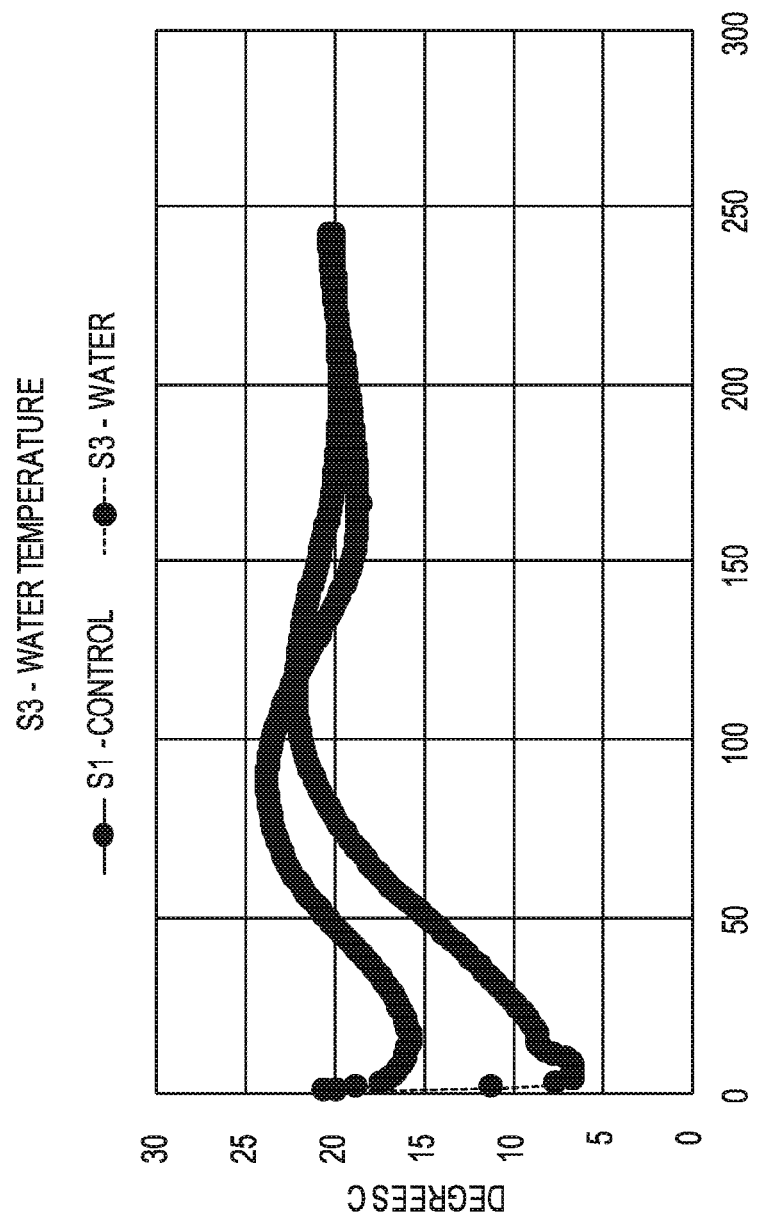
FIGS. 10 and 11 are graphs plotting actual fluid temperature (S3) and temperature measurements taken from a first temperature sensor (S1) in proximity to the sample chamber.
Figure 11:
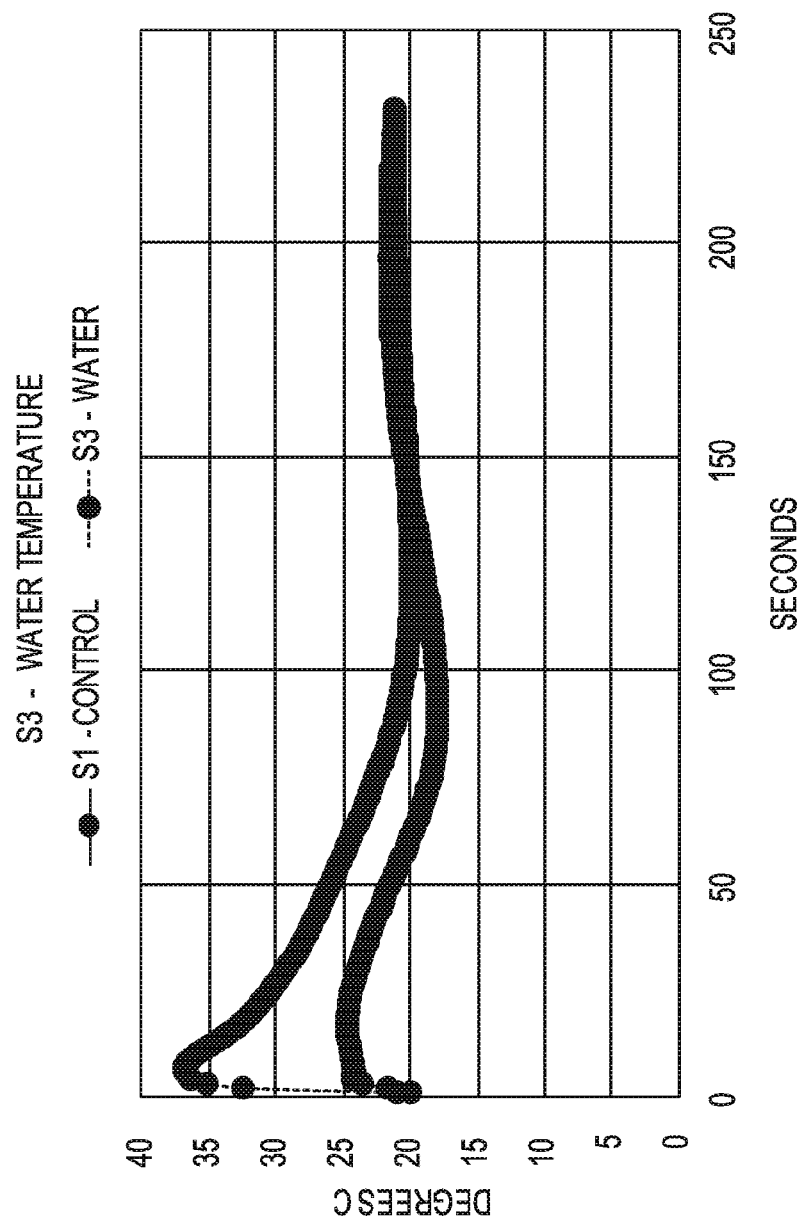
Figure 12:
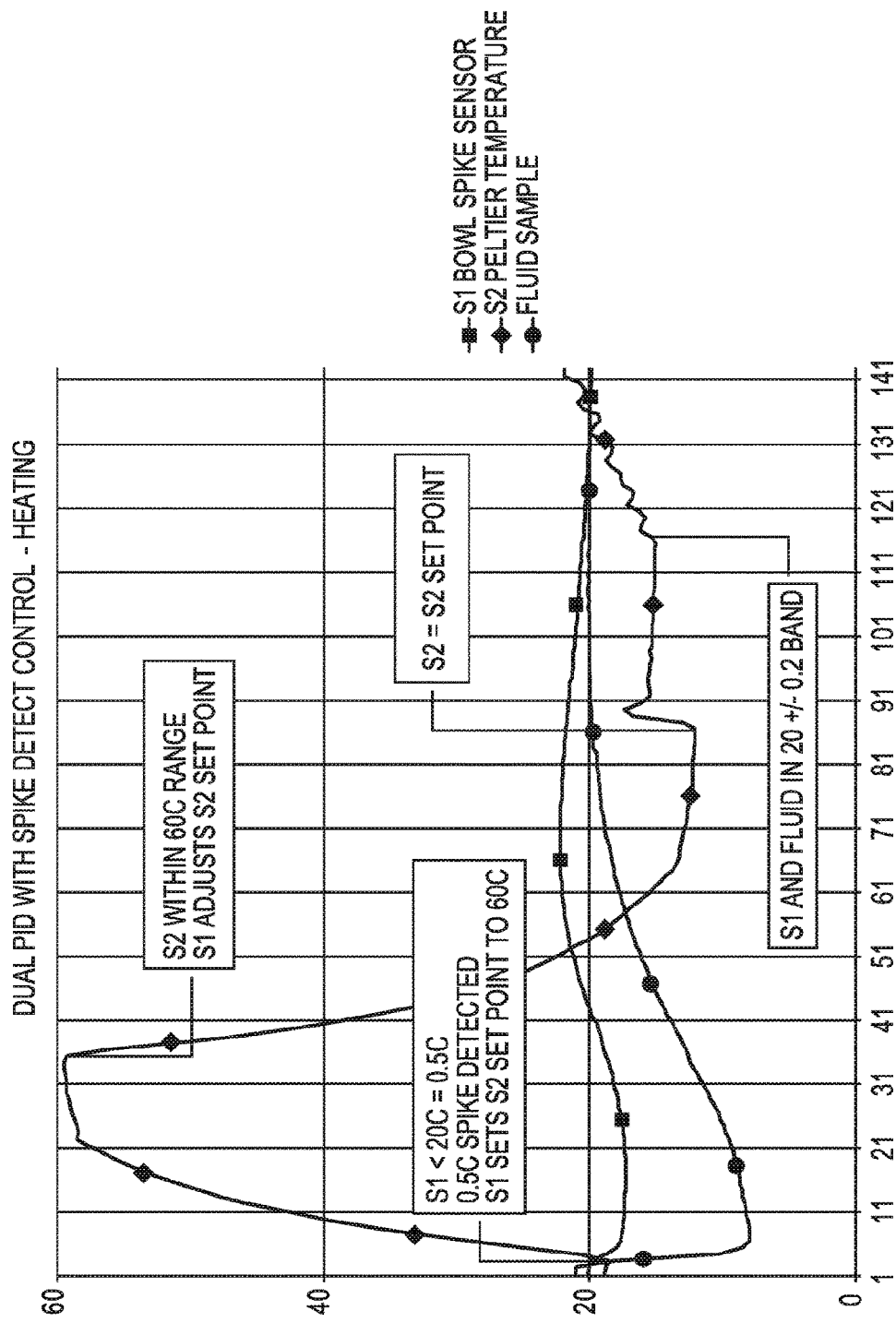
FIGS. 12 and 13 are graphs plotting actual fluid temperature (S3), temperature measured at a first temperature sensor (S1) in proximity to the sample chamber and a second fluid sensor (S2) in proximity to a heating/cooling element.
Figure 13:
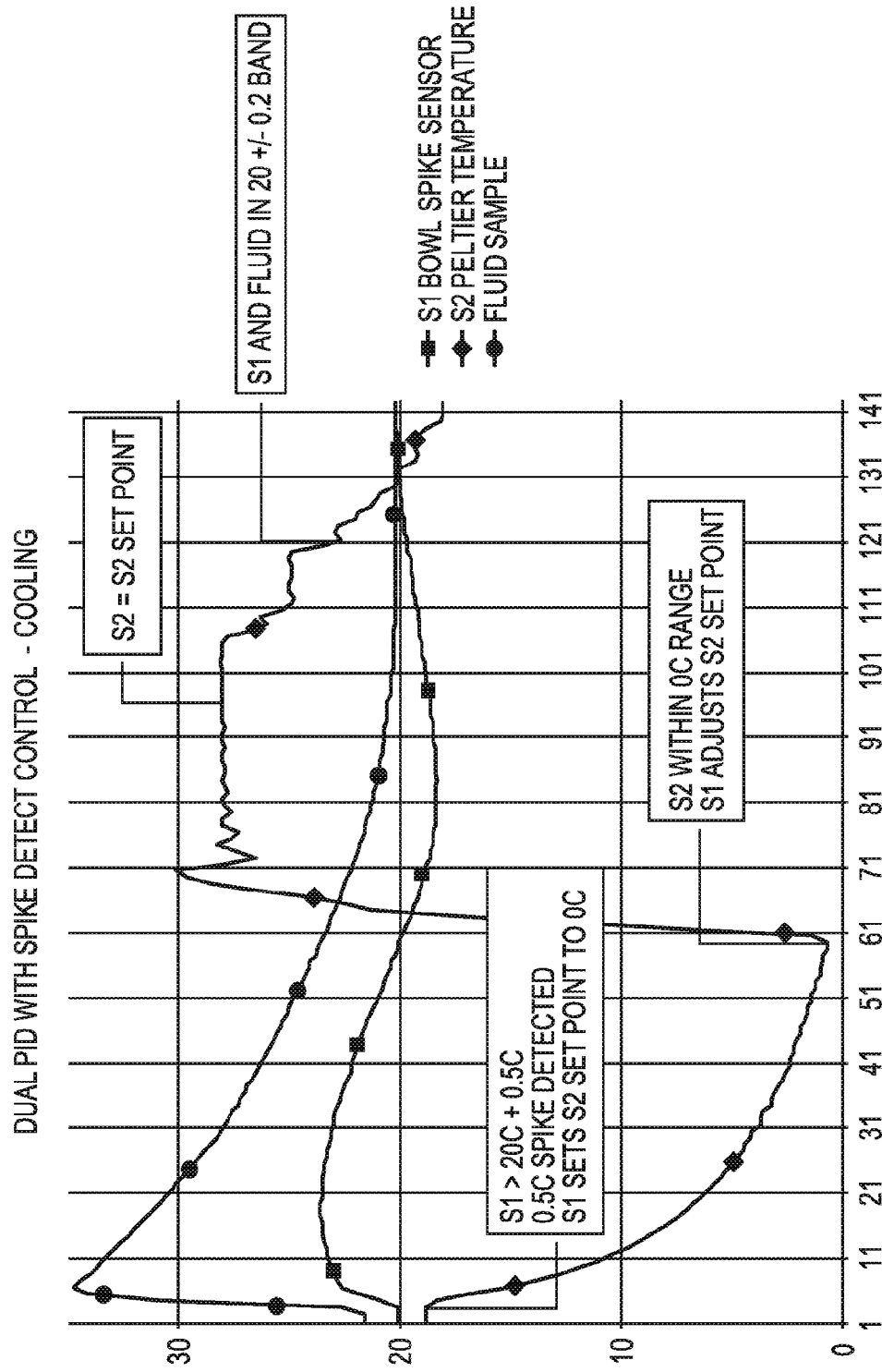

The temperature of the sample in the sample chamber 210 in scenarios where spike mode controller (SMC) 274 is activated followed by dual PID mode controller 272 to control the temperature of a sample in sample chamber 210 may be better understood with reference to FIGS. 10 and 11 which depict graphs taken in conjunction with embodiments of an operational sensor system 200 plotting actual fluid temperature (S3), temperature measured at a first temperature sensor 262 (S1) in proximity to the sample chamber 210 and a second fluid sensor 262 (S2) in proximity to a heating/cooling element 240, where temperature is plotted on the Y axis and time is plotted on the X axis.

Figure 3A:
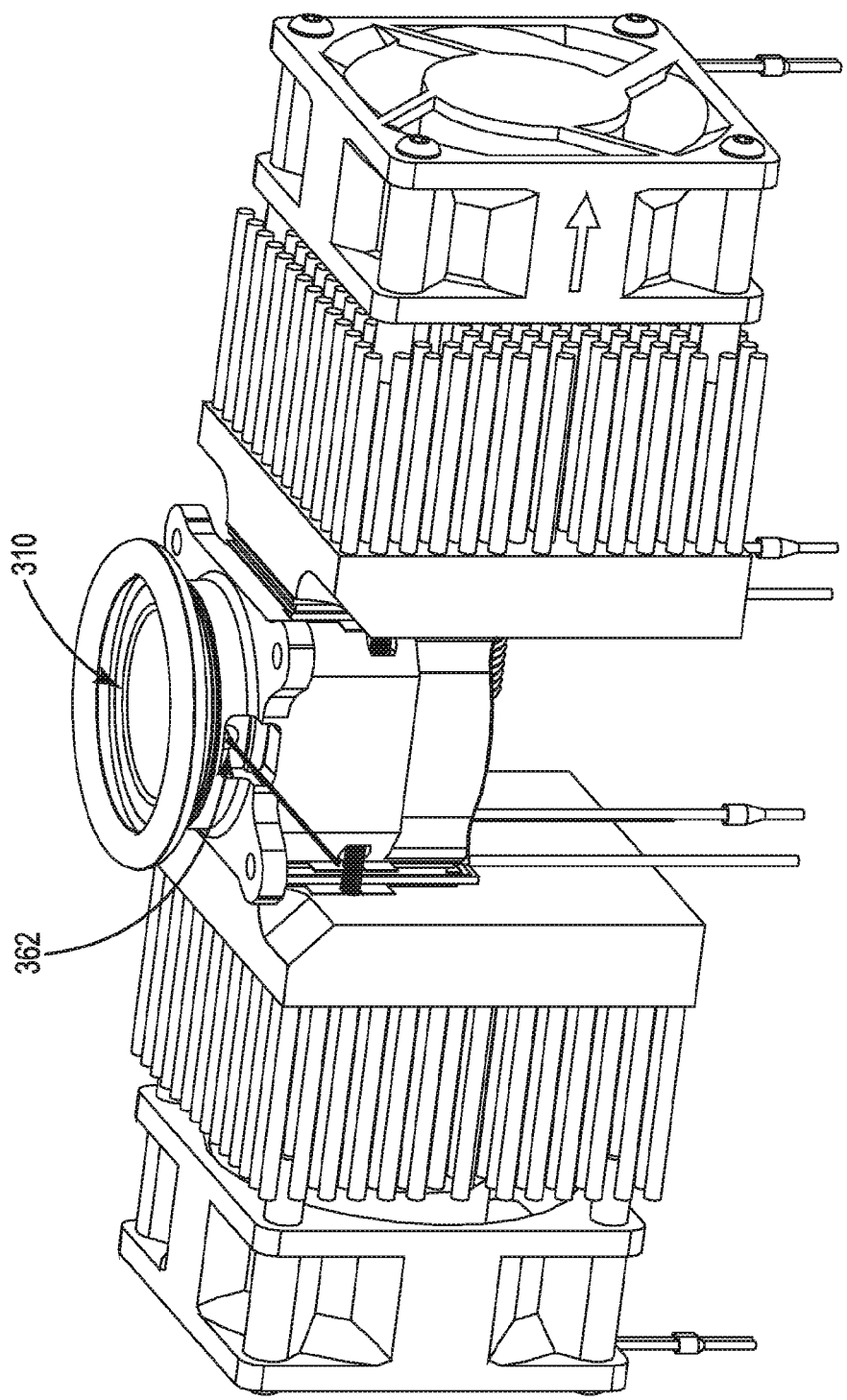
Figure 3B:
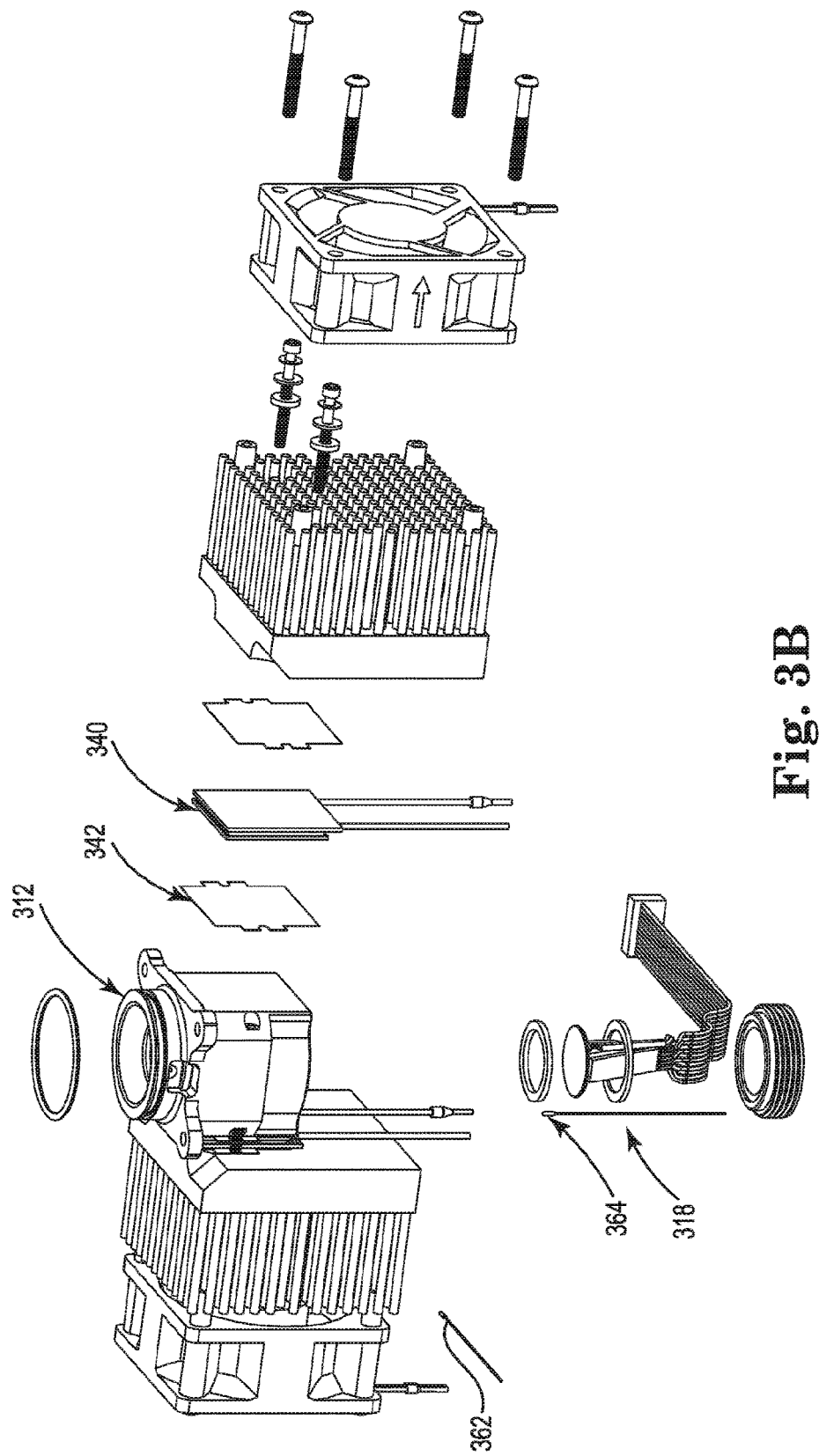

Looking now at FIGS. 3A, 3B and 3c, embodiments of a bowl assembly 312 with a sample chamber 310 are depicted. As is illustrated, IoR sensor 318 interfaces with sample chamber 310 in bowl assembly 312 via an optical window included in sensor 318. Heating/cooling elements 340 comprising a Peltier device may be thermally coupled to bowl assembly 312 using screws and a graphite pad 342 may be disposed between the element 340 and the bowl assembly 312. First temperature sensor 362 (S1) may be disposed in proximity to sample chamber 310 of bowl assembly 312 while second temperature sensor 364 (S2) may be disposed in a trough or channel 368 formed in the surface 366 of bowl assembly 312 between element 340 and bowl assembly 312.

Figure 4:
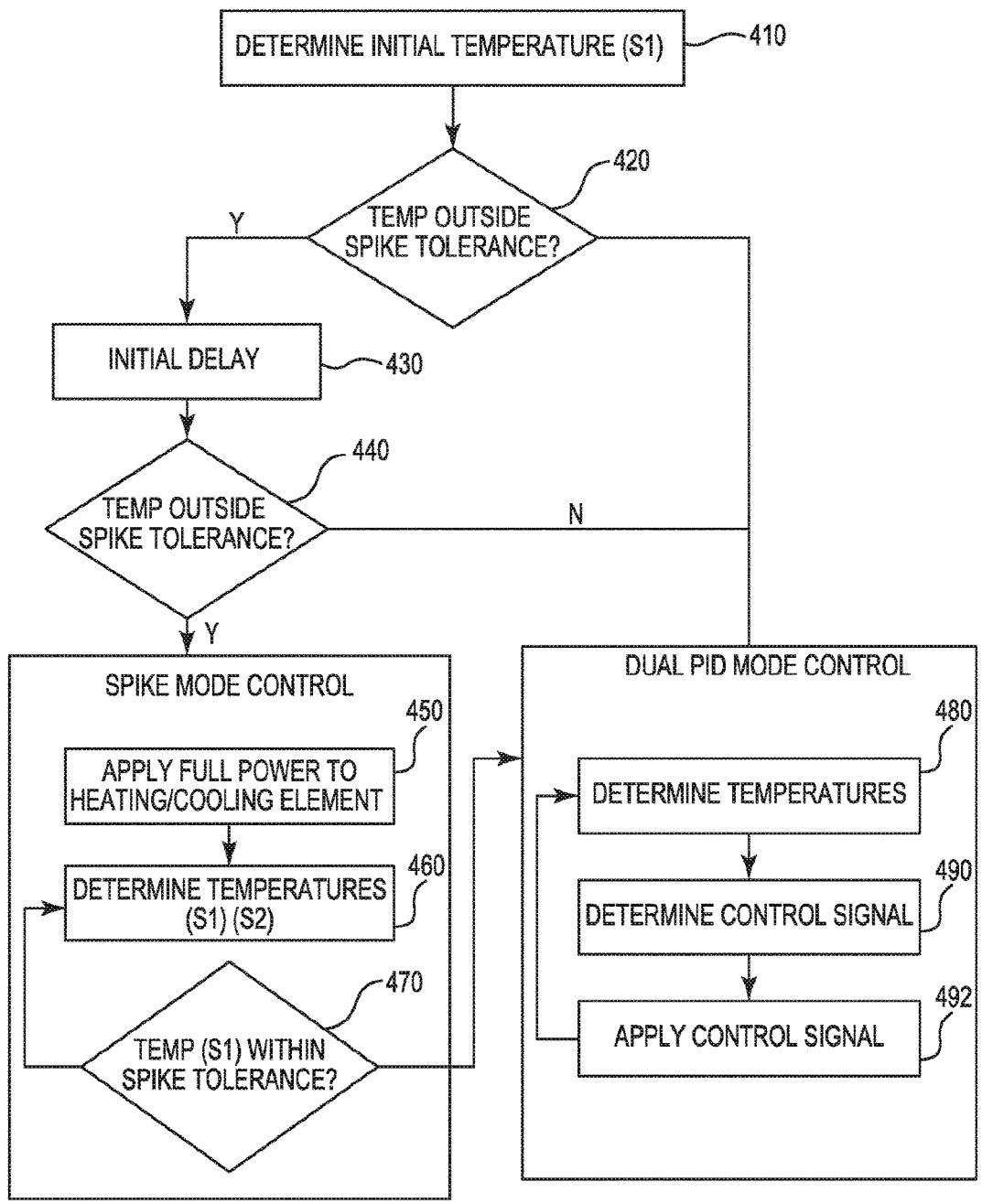
FIG. 4 is a flow diagram of a method for temperature control for use in a sensor system in accordance with an embodiment of the disclosure.

FIG. 4 depicts one embodiment of a method for temperature control for use with embodiments of sensor systems described herein. Initially at step 410 an initial temperature measurement may be obtained from the first temperature sensor (S1) nearest the sample chamber of the sensor system. At step 420 it can be determined if this temperature is outside the spike tolerance of the sampling temperature setpoint. To illustrate a specific example, it can be determined if the measured temperature at S1 is within 0.5 degrees Celsius (the spike tolerance) of 20 degrees Celsius (the sampling temperature setpoint). If the first measured temperature does not exceeds the spike tolerance (e.g., is not hotter than 20.5 degrees Celsius or colder than 19.5 degrees Celsius) the dual PID control mode may be entered at step 480.

If, however, the first measured temperature exceeds the spike tolerance (e.g., is hotter than 20.5 degrees Celsius or colder than 19.5 degrees Celsius) a delay time period (which may be two seconds though other time periods are possible) may be initiated at step 430 to ensure that the first measured temperature is not an artifact or noise. It will be noted that such a delay time period is optional and may not be utilized in other embodiments. After this delay time period has elapsed at step 430, another first temperature measurement from the from the first temperature sensor (S1) may be determined and at step 440 it can again be determined if this first measured temperature is outside the spike tolerance of the sampling temperature setpoint. If the first measured temperature does not exceed the spike tolerance the dual PID control mode may be entered at step 480. However, if the first measured temperature again exceeds the spike tolerance at step 440, spike mode may be entered at step 450. In spike mode the dual PID control of the heating/cooling elements of the sensor system may be set to a high or maximum current in a particular direction. High or full power (e.g., high or maximum current in a particular direction) is applied at step 450 to the heating or cooling element to drive them to a high or their maximum cold temperature (in the case where the first temperature measurement is greater than the sampling temperature setpoint plus the spike tolerance) or high or maximum hot temperature (in the case where the first temperature measurement is less than the sampling temperature setpoint minus the spike tolerance).

The temperature at the heating/cooling elements can be determined at certain time intervals (e.g., one second or the like) at step 460 by determining a second temperature measure from the second temperature sensor (S2) between the heating/cooling elements and the bowl assembly. As the second temperature sensor (S2) is close to the heating/cooling element itself this position may minimize the lag in making such a determination. By making such a temperature determination at step 460 it can be determined that the heating/cooling elements are indeed being driven to their high or maximum setpoints or that such a high or maximum setpoint has been reached. Additionally, at step 460 in some embodiments a first temperature measure from the first temperature sensor (S1) may also be determined. This temperature (or these temperatures) at the first temperature sensor or second temperature sensor can be determined until at step 470 a determination that the first temperature measured at the first temperature sensor (S1) is within the spike tolerance of the sampling temperature setpoint. Once such a determination that the first temperature is within the spike tolerance of the sampling temperature setpoint is made, the dual PID mode control may be enabled at step 480 and allowed to control the heating/cooling elements of the system to substantially maintain the desired sampling temperature setpoint within the sampling tolerance.

At step 480 then, at some interval a first temperature measured at the first temperature sensor (S1) and a second temperature measured at the second temperature sensor (S2) may be determined. Using these temperatures and other data, including the measurement temperature setpoint, a control signal for heating/cooling can be determined at step 490. The determined control signal may then be provided to the heating/cooling elements at step 492 to maintain the desired sampling temperature setpoint within the sampling window (e.g., 20 degrees Celsius plus or minus 0.2 degrees Celsius).

Figure 5:
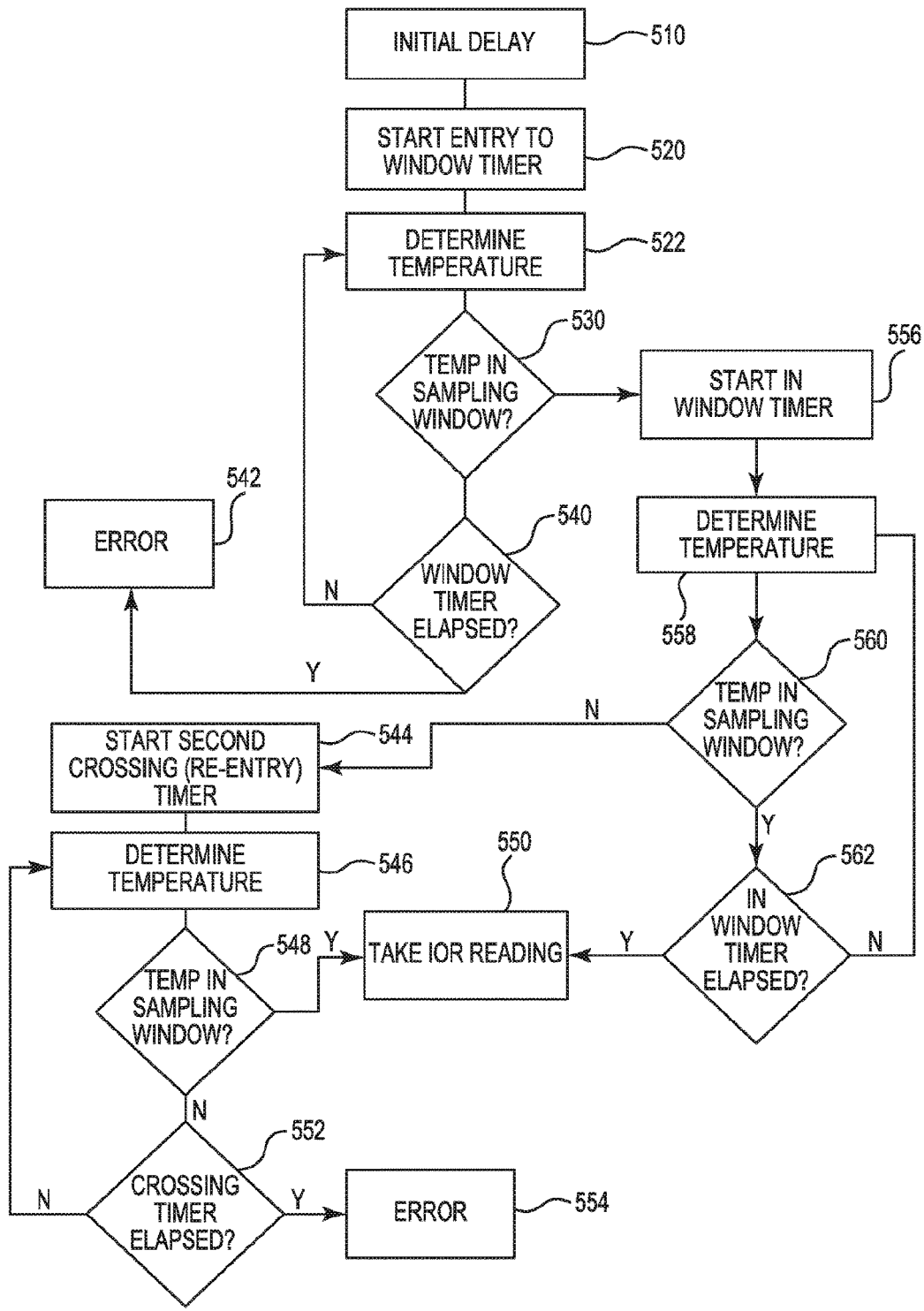
FIGS. 5 and 6 are flow diagrams of methods for obtaining an IoR measurement for use in a sensor system in accordance with embodiments of the disclosure.

Moving now to FIG. 5, one embodiment of a method for IoR measurement for use with embodiments of sensor systems as described herein, such as with reference to FIG.

2, is depicted. Embodiments of this method may, for example, be utilized when an operator of a sensor system initiates or otherwise indicates that an IoR measurement is desired. Initially, an optional delay time period or waiting period may be allowed to elapse to ensure the sensor system is in a steady state at step 510. In some cases, the initial delay time period may range from 10 seconds to 5 minutes. In one example, the initial time delay period may be 5 minutes. In other examples, the initial time delay is less than 5 minutes, less than 3 minutes and more particularly, less than 1 minute. Once this initial delay period (if any) has been allowed to elapse, a window timer may be started at step 520. This window timer may be to ensure that a first temperature measurement at a first temperature sensor (S1) enters the sampling temperature window (e.g., the sampling temperature setpoint plus or minus the sampling tolerance) within a certain time period. This time period may be, for example, around 120 seconds or the like though other time periods are possible and contemplated. During this window time period a first temperature measurement at the first temperature sensor (S1) can be determined at step 522 and compared to the sampling window to determine if the measured temperature at the first temperature sensor (S1) is within the sampling window (e.g., 20 degrees Celsius plus or minus 0.2 degrees Celsius to continue with the above example). This temperature measurement at step 522 and determination at step 530 can be continued until a determination is made at step 540 that the window timer has elapsed at step 540 (e.g., without the first temperature measurement ever entering the sampling window). In this case, an error may be reported an operator or other action taken at step 542.

If the first temperature as measured at the first temperature sensor (S1) is within the sampling window at step 520 an In Window timer may started at step 556. This In Window timer may be to ensure that a first temperature measurement at a first temperature sensor (S1) remains within the sampling temperature window (e.g., the sampling temperature setpoint plus or minus the sampling tolerance) for a certain time period before an IoR measurement is taken. This In Window time period may be, for example, around 45 seconds or the like though other time periods are possible and contemplated. During this In Window time period a first temperature measurement at the first temperature sensor (S1) can be determined at step 558 and compared to the sampling window to determine if the measured temperature at the first temperature sensor (S1) is within the sampling window. This temperature measurement at step 558 and determination at step 560 can be continued until a determination is made at step 562 that the In Window timer has elapsed (e.g., without the first temperature measurement ever exiting the sampling window). In this case, an IoR measurement is taken using the IoR sensor of the system at step 542 and reported to the operator.

If the first temperature as measured at the first temperature sensor (S1) is outside the sampling window at step 560 a second crossing timer may started at step 544. This second crossing timer may be to ensure that a first temperature measurement at a first temperature sensor (S1) comes back within the sampling temperature window (e.g., the sampling temperature setpoint plus or minus the sampling tolerance) within a certain time period. This second crossing time period may, for instance 180 seconds, though other time periods are contemplated. This second crossing timer may be desired because of certain characteristics of the sensor system. In particular, in many cases, especially where spike mode has been initially implemented in conjunction with temperature control of the sensor system when the first temperature measurement as measured at the first temperature sensor (S1) initially enters the sampling window the actual temperature of the fluid sample may be not be a desired temperature for taking an IoR measurement. In these embodiments, it may be that the actual temperature of the fluid sample is within the sampling tolerance when the first temperature measurement as measured at the first temperature sensor (S1) comes back within the sampling window (e.g., for a second time). In other words, in some embodiments the second crossing (or entrance) of the first measured temperature at the first temperature sensor (S1) may be the first time the actual temperature of the fluid sample is within the sampling window. This scenario may be better understood with reference to FIGS. 8 and 9 which depict a graph of actual fluid sample temperature (S3) versus temperature as measured at a first temperature sensor (S1).

Referring to FIG. 5 again, during this second crossing time period a first temperature measurement at the first temperature sensor (S1) can be determined at step 546 and compared to the sampling window at step 548 to determine if the measured temperature at the first temperature sensor (S1) is back within the sampling window. This temperature measurement at step 546 and determination at step 548 can be continued until a determination is made at step 552 that the second crossing timer has elapsed (e.g., without the first temperature measurement ever re-entering the sampling window). In this case an error may be reported back to an operator or another action taken at step 554. When it is determined at step 548 that the first measured temperature at the first temperature sensor (S1) is back within the sampling window an IoR measurement is taken using the IoR sensor of the system at step 542 and reported to the operator.

Figure 6:
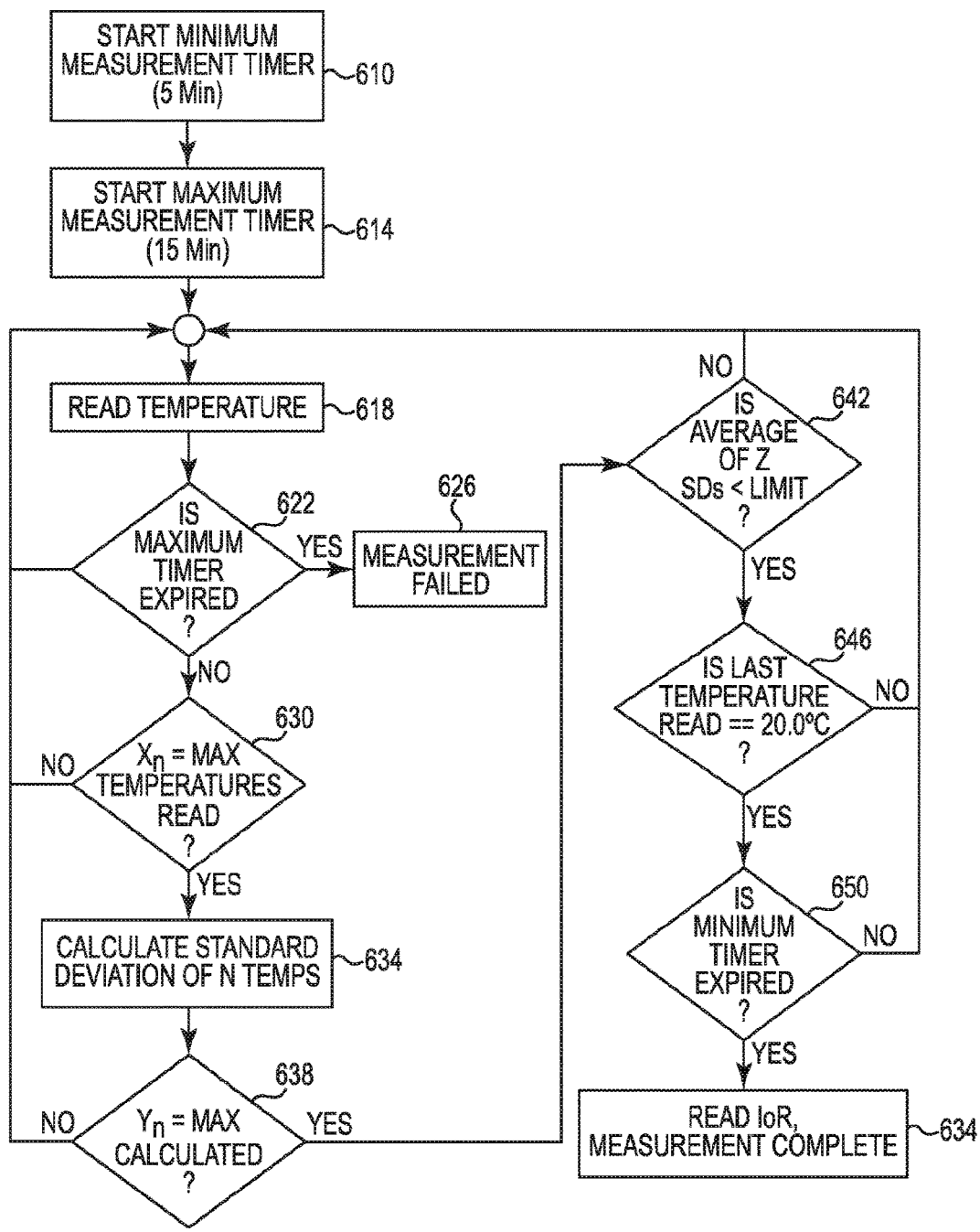

FIG. 6 outlines another method for IoR measurement for use with embodiments of sensor systems such as described herein with reference to FIG. 2 is depicted. Embodiments of this method may, for example, be utilized when an operator of a sensor system initiates or otherwise indicates that an IoR measurement is desired. Initially, an optional delay time period or waiting period may be allowed to elapse by setting as starting a minimum measurement timer at step 610 to ensure the sensor system is in a steady state prior to a measurement being taken. In some cases, the initial delay time period may range from 10 seconds to 5 minutes. In one example, the initial time delay period may be 5 minutes. In other examples, the initial time delay is less than 5 minutes, less than 3 minutes and more particularly, less than 1 minute. A maximum window timer may be started at step 614. The final temperature should be read prior to the maximum time set at step 614 expires. Together, the minimum measurement timer and the maximum timer determine a window time period during which a number of temperature measurements can be obtained using a temperature sensor, such as temperature sensor 262, coupled to the chamber. The temperature of the sample chamber is obtained at step 618. At step 622, if the maximum time set at step 614 has been exceed, then the temperature measurement fails. However, if the maxim amount of time set at step 614 has not yet expired, then a number of temperature measurements can be sampled until the number of temperature measurements reaches a predetermine maximum as determined by step 630. Once a predetermined maximum number of temperature measurements has been reached, the standard deviation of the temperature measurements is calculated at step 634. This calculation is related until a predetermined number of standard deviations is calculated at step 638. An average standard deviation is then determined at 642. If the average standard deviation is greater than a predetermined limit, then the controller returns to step 618. If the average standard deviation is less than a predetermined limit, then the controller proceeds to step 646. At step 646, if the last temperature read by the temperature sensor is not substantially equal to a predetermined value (e.g. 20° C.) then the controller return to step 618 and steps 618-642 are repeated as necessary. If, at step 646, the last temperature read by the temperature sensor is substantially equal to a predetermined value (e.g. 20° C.) then the controller proceeds to step 650. If at step 650, the controller determine that a minimum time as set at step 610 has expired, then the controller sends a command to the IoR sensor to take measure the IoR of the sample at step 660.

Figure 7:
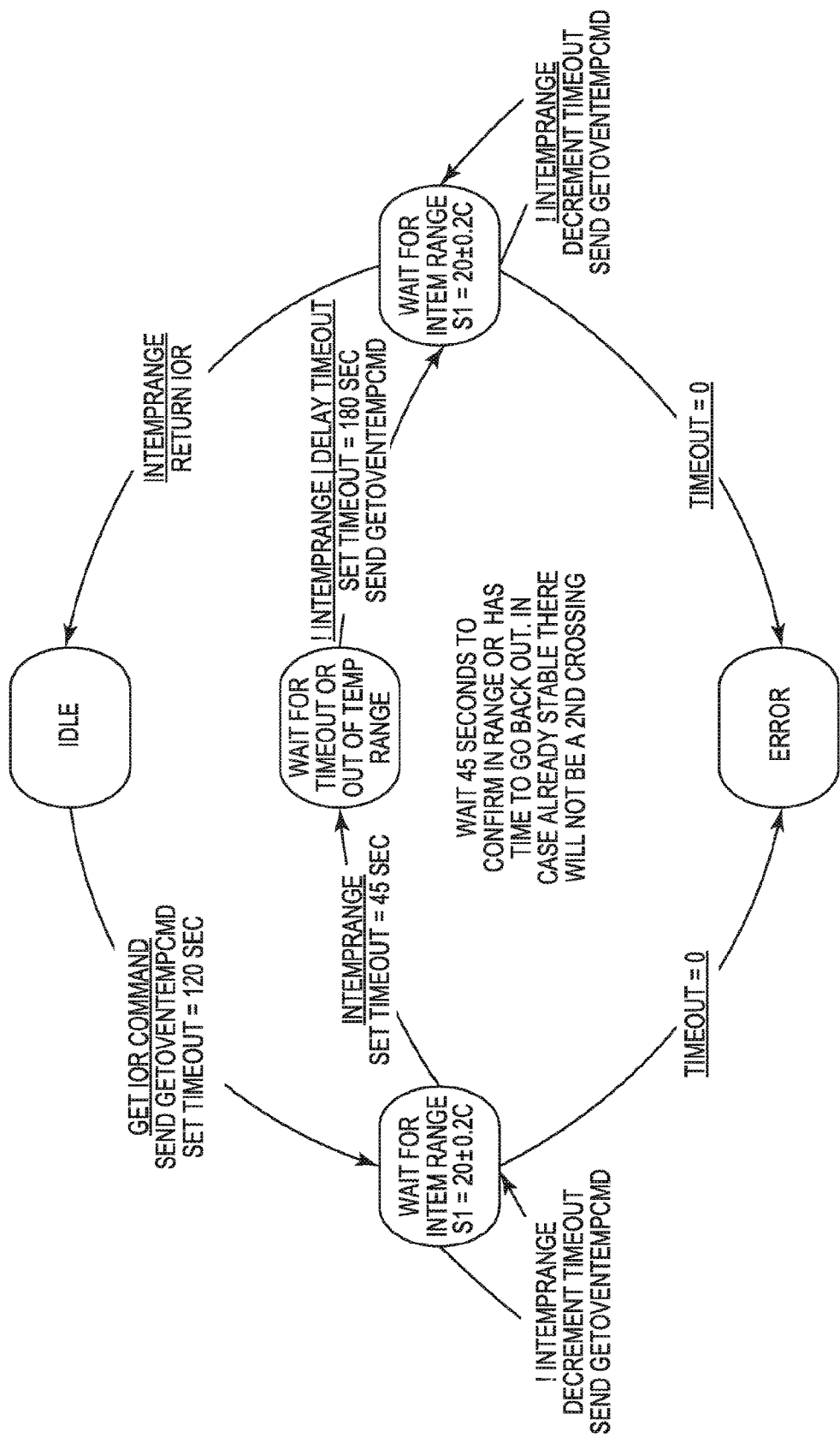
FIGS. 7-9 are state diagrams representing embodiments for obtaining an IoR measurement for use in a sensor system.
Figure 8:
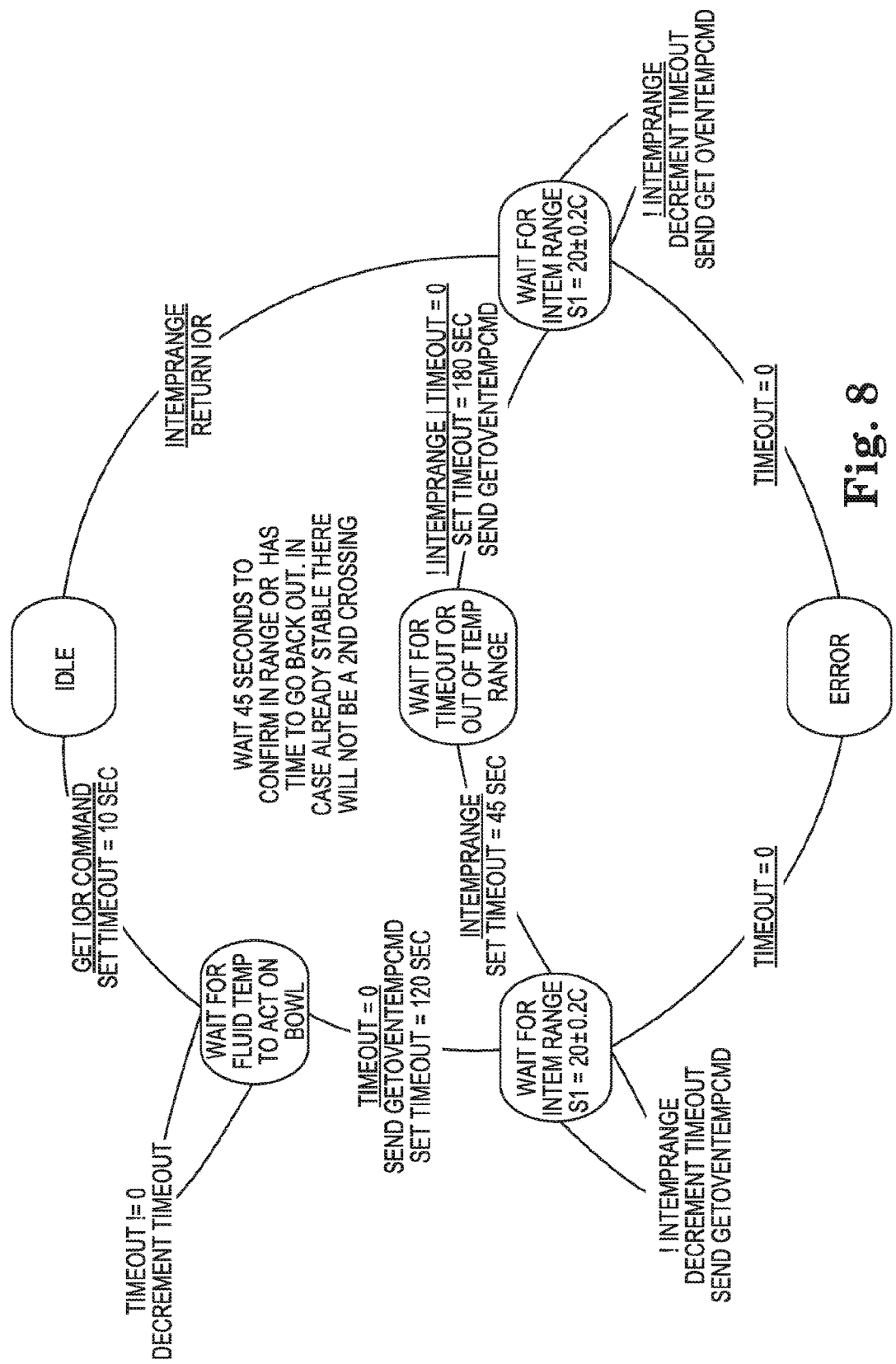
Figure 9:
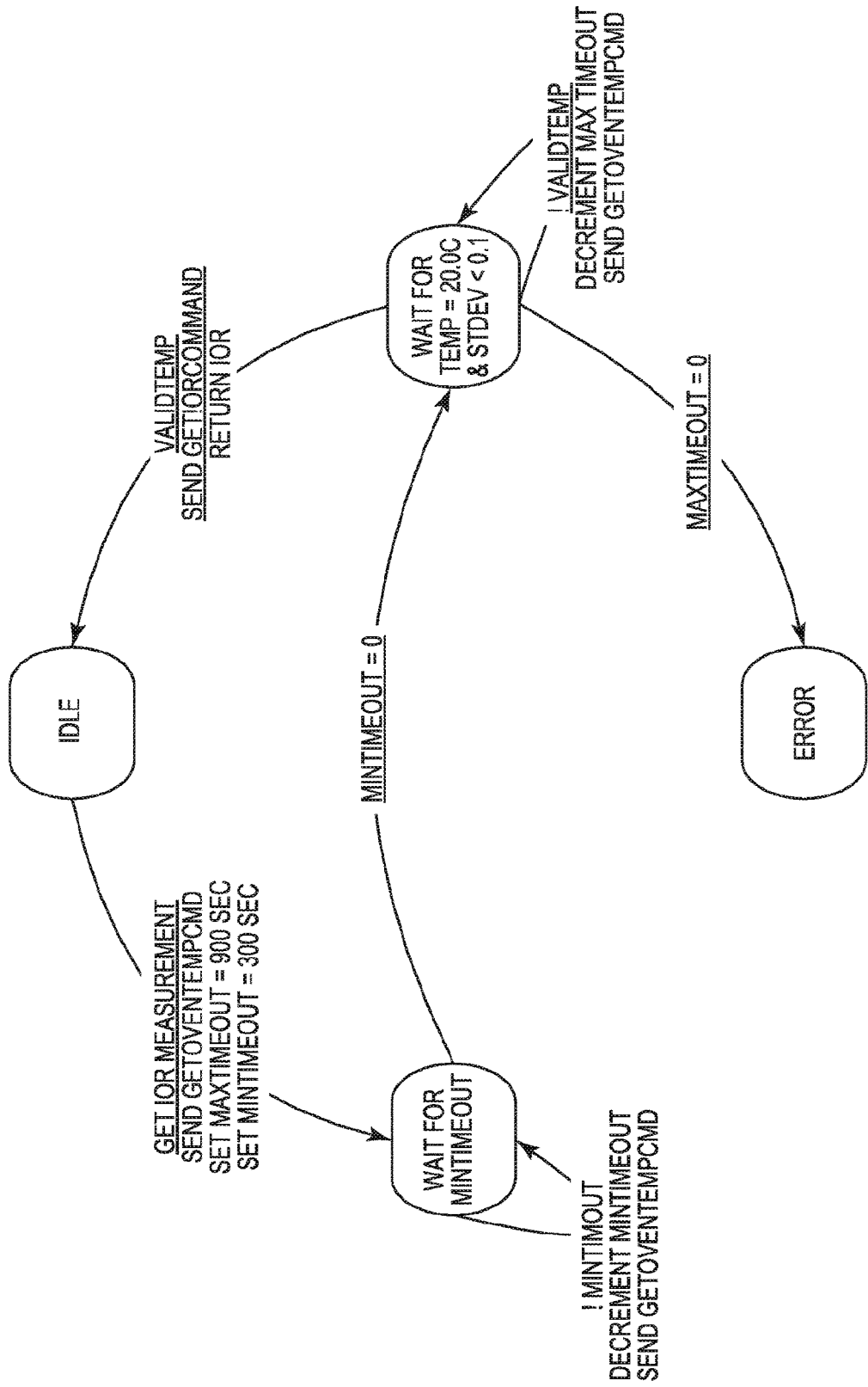

Embodiments may be better understood with reference to FIGS. 7-9 which depict state diagrams for embodiments of determining an IoR measurement according to embodiments of sensor systems described herein. One example of how to collect sensor data is described in U.S. Pat. No. 7,319,523 filed on Sep. 26, 2005 by Chiarello et al, which is hereby fully incorporated herein by reference in its entirety for all purposes.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The disclosure's scope is, of course, defined in the language in which the appended claims are expressed

What is claimed is:

1. A sensor system for measuring the index of refraction of a sample, the sensor system comprising:
    a sample chamber for receiving a sample;
    a first temperature sensor coupled to the sample chamber;
    one or more heating and cooling elements coupled to the sample chamber;
    an index of refraction sensor exposed to the sample chamber, the sample chamber having a sampling temperature setpoint; and
    a system controller comprising a memory having the sampling temperature setpoint of the sample chamber stored therein, and a spike mode controller (SMC), the system controller electronically coupled to and in communication with the first temperature sensor, the one or more heating and cooling elements and the index of refraction sensor, wherein if the system controller determines that a temperature of the sample chamber is outside the sampling temperature setpoint as measured by the first temperature sensor, the system controller is configured to activate the spike mode controller (SMC) to operate one or more heating and cooling elements to rapidly bring the temperature of the sample within the sampling temperature setpoint of the index of refraction sensor as determined by the first temperature sensor.

2. The sensor system of claim 1, wherein the spike mode controller (SMC) operates the one or more heating and cooling elements to a maximum hot setpoint or a maximum cold setpoint.

3. The sensor system of claim 1, wherein the system controller further comprises a PID controller, wherein if the system controller determines that the temperature of the sample chamber as determined by the first temperature sensor is within the sampling temperature setpoint, the system controller is configured to activate the PID mode controller to maintain the temperature of the sample within the sampling temperature setpoint.

4. The sensor system of claim 3, wherein the system controller operates the spike mode controller (SMC) to send a control signal to the one or more heating and cooling elements to drive the heating and cooling element to a maximum cold or maximum hot setpoint as determined by a second temperature sensor coupled to the heating and cooling element, wherein when the temperature as measured by the first temperature sensor falls within the sampling temperature setpoint, the system controller then operates the PID mode controller to operate the one or more heating and cooling elements to maintain the temperature of the sample chamber within the sampling temperature setpoint.

5. The sensor system of claim 3, wherein in response to receiving a signal from the first temperature indicating that the temperature of the sample is within the sampling temperature setpoint, the system controller is further configured to operate the index of refraction sensor to take a measurement of the sample.

6. The sensor system of claim 1, wherein in response to receiving a signal from the first temperature sensor indicating that the temperature of the sample is within the sampling temperature setpoint, the system controller is further configured to initiate a waiting period, wherein after the waiting period expires, the system controller is configured to operate the index of refraction sensor to take a measurement of the sample.

7. The sensor system of claim 3, further comprising a second sensor coupled to the one or more heating and cooling elements, wherein the PID mode controller is configured to sample temperature measurements received from the first temperature sensor coupled to the sample chamber and the second temperature sensor, the PID mode controller further configured to derive a control signal for controlling the one or more heating elements based on the temperatures and the sampling temperature setpoint and to transmit the control signal to the heating and cooling elements to maintain the temperature of the sample chamber within the sampling temperature setpoint.

8. The sensor system of claim 1, wherein the sampling temperature setpoint has a tolerance and wherein if the system controller determines that a temperature of the sample is outside the tolerance of the sampling temperature setpoint as measured by the first temperature sensor, the system controller is configured to activate the spike mode controller (SMC) to operate one or more heating and cooling to reach a maximum hot or a maximum cold temperature to rapidly bring the temperature of the sample within the tolerance of sample temperature setpoint as determined by the first temperature sensor.

9. The sensor system of claim 1, further comprising a second temperature sensor coupled to the one or more heating and cooling elements.

10. The sensor system of claim 1, further comprising an interface port for communicating with an external computing device.

11. A method of measuring the index of refraction of a sample, the method comprising:
    receiving a sample in a sampling chamber of sensor system, the sensor system comprising a system controller in electronic communication with first temperature sensor coupled to the sample chamber, one or more heating and cooling elements coupled to the sample chamber, and an index of refraction sensor exposed to the sample chamber, the system controller comprising a spike mode controller (SMC) and a PID mode controller;

measuring a temperature of the sample via the temperature sensor;

determining if the temperature of the sample chamber is within a sampling temperature setpoint, activating a spike mode controller (SMC) to operate one or more heating and cooling to reach a maximum hot or a maximum cold temperature if the system controller determines that a temperature of the sample is outside the sampling temperature setpoint as measured by the temperature sensor;

activating a PID mode controller to maintain the temperature of the sample within the sampling temperature setpoint if the system determines that the temperature of the sample is within the sampling temperature setpoint as measured by the first temperature setpoint; and measuring an index of refraction of the sample when the temperature of the sample is within the sampling temperature setpoint.

12. The method of claim 11, further comprising operating the one or more heating and cooling elements to a maximum hot setpoint if the system controller determines that the temperature of the sample chamber is below the sampling temperature setpoint to rapidly increase the temperature of the sample as measured by the temperature sensor.

13. The method of claim 11, further comprising operating the one or more heating and cooling elements to a maximum cold setpoint in response to the system controller determining that the temperature of the sample is above the sampling temperature setpoint to rapidly decrease the temperature of the sample chamber as measured by the temperature sensor.

14. The method of claim 11, further comprising the system controller initiating a waiting period prior to measuring an index of refraction of the sample when the temperature of the sample chamber is within the sampling temperature setpoint.

15. The method of claim 11, wherein the spike mode controller (SMC) is activated until the temperature of the sample chamber is within the sampling temperature range after which the PID mode controller is activated to maintain the temperature of the sample chamber within the sampling temperature range.

* * * * *